(12) United States Patent
Ramsey

(10) Patent No.: US 6,168,955 B1
(45) Date of Patent: Jan. 2, 2001

(54) ANALYTICAL APPARATUS

(75) Inventor: Edward Ramsey, Lakeside (GB)

(73) Assignee: University of Glamorgam Commercial Services Limited, Pontypridd (GB)

( * ) Notice: Under 35 U.S.C. 154(b), the term of this patent shall be extended for 0 days.

(21) Appl. No.: 09/111,164

(22) Filed: Jul. 7, 1998

Related U.S. Application Data

(63) Continuation-in-part of application No. PCT/GB97/00047, filed on Jan. 8, 1997, now abandoned.

(30) Foreign Application Priority Data

Jan. 8, 1996 (GB) .................................................. 9600461

(51) Int. Cl.$^7$ ...................................................... G01N 1/34
(52) U.S. Cl. ...................... 436/178; 210/634; 422/82.05; 422/101; 436/139; 436/164
(58) Field of Search ............................... 422/82.05, 101; 436/164, 178, 139; 210/787, 634, 511

(56) References Cited

U.S. PATENT DOCUMENTS 4,960,221 * 10/1990 Hiraoka et al. .
5,116,508 * 5/1992 Kumar et al. .

FOREIGN PATENT DOCUMENTS

| | | |
|---|---|---|
| 0522988 | 1/1993 | (EP) . |
| 9206058 | 4/1992 | (WO) . |
| 9323737 | 11/1993 | (WO) . |

OTHER PUBLICATIONS

Jordan et al., Textile Research Journal, vol. 64, No. 4, pp. 230–235, Apr. 1995.

J. Ezzell and B. Richter, "Supercritical Fluid Extraction of Pesticides and Phthalate Esters Following Solids Phase Extraction from Water," *J. Microcol. Sep.* 4 319–323 (1992).

J. Hedrick, L. Mulcahey, and L. Taylor, "Supercritical Fluid Extraction of Phenols From Water," *Supercritical Fluid Technology* 206–220 (1992).

B. Minty et al., "Analysis of oil in water at the low ppm level using direct supercritical fluid extraction coupled on–line with infrared spectroscopy," *35 Anal. Commun.* 277–280 (1998).

Selected pages of Revision 1.3 "Supercritical Fluid Chromatograph Operating Manual," published Jan. 18, 1988 by Suprex Corporation, Pittsburgh, PA 15238.

Keystone Scientific, Inc. brochure obtained by Applicant from sales representative Keith Coleman, Anachem, Luton, United Kingdom in 1996.

Suprex SFE Systems brochure regarding Suprex SFE marketed from 1993–1997 obtained at scientific conference stand by Applicant.

Analytical Chemistry, vol. 65, No. 1, Jan. 1, 1993, USA, pp. 78–83, XP000653339 C.H. Kirschner, L:T:Taylor: "Quantitative Analysis by On–Line Supercritical Fluid Extraction/ Fourier Transform Infrared Spectrometry" see the whole document.

Angewandte Chemie (International Edition in English), Jul. 7, 1995, VCH Verlagsgesellschaft, Germany, vol. 34, No. 12, ISSN 0570–0833,pp. 1275–1295, XP000652040 Poliakoff M et al: "Vibrational Spectroscopy in Supercritical Fluids: From Analysis and Hydrogen Bonding to Polymers and Synthesis" see the whole document.

Analytical Chemistry, vol. 66, No. 12, Jun. 15, 1994, USA, pp. 106R–130R, XP000653196 T.L. Chester et al: "Supercritical Fluid Chromatography and Extraction" cited in the application see p. 121R, paragraph 2.

* cited by examiner

*Primary Examiner*—Jan Ludlow
(74) *Attorney, Agent, or Firm*—Vinson & Elkins L.L.P.

(57) ABSTRACT

Analytical apparatus which may be used for monitoring compounds present in a fluid, and a method of analysis. Compounds are extracted from the fluid sample in an extraction chamber by means of a supercritical fluid and analyzed in an analysis cell, which is in direct communication with the extraction cell.

25 Claims, 1 Drawing Sheet

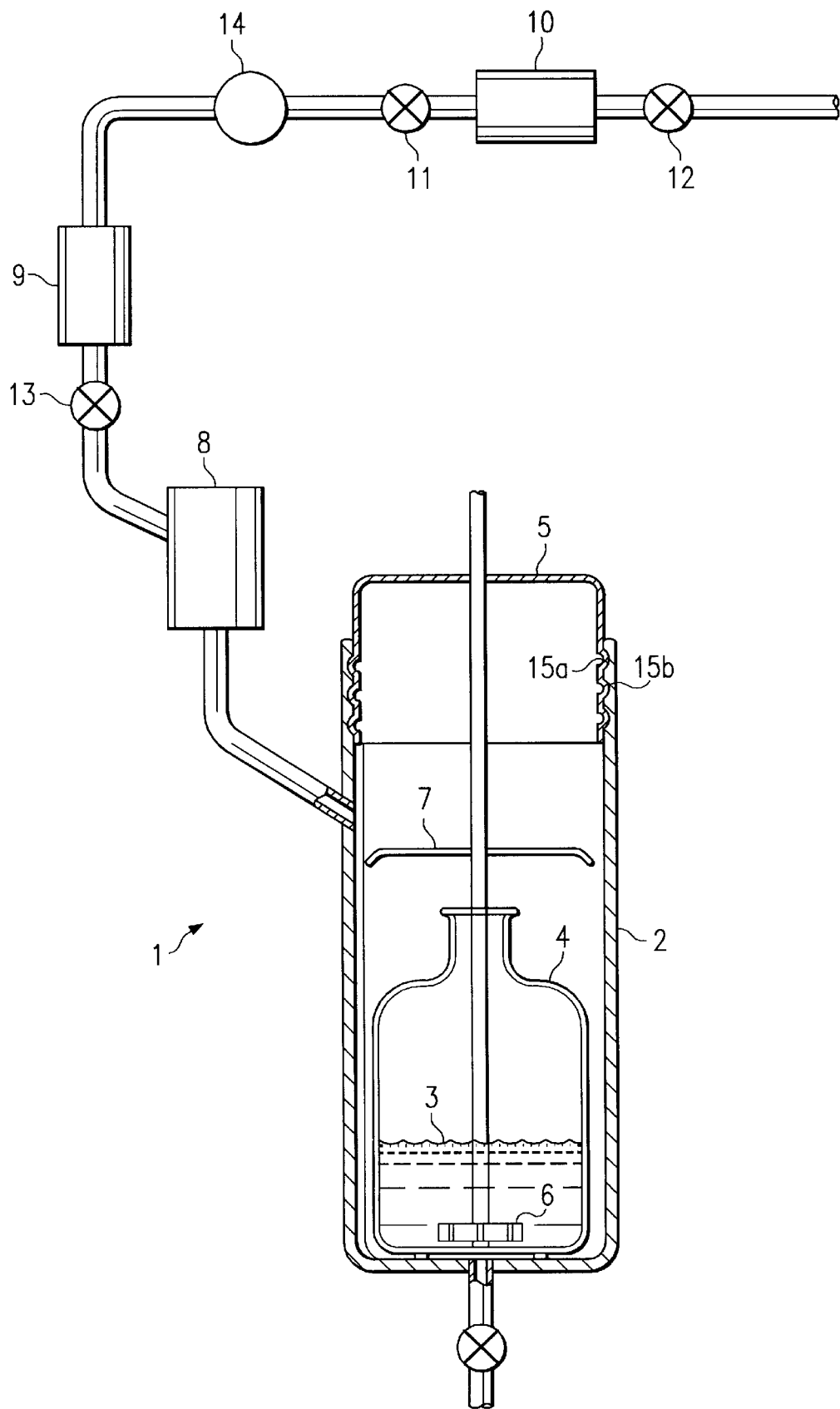

ANALYTICAL APPARATUS

This is a continuation-in-part application of International Application PCT/GB97/00047, with an international filing date of Jan. 8, 1997, now abandoned, which was an international filing of foreign priority application 9600461.9 filed on Jan. 8, 1996 in the United Kingdom. The disclosure of both of said applications are incorporated herein by reference.

BACKGROUND OF THE INVENTION

The present invention relates to analytical apparatus and in particular to apparatus for monitoring compounds present in a fluid, and a method of analysis.

Typically in, for example, the petrochemical or steel manufacturing industries, it is necessary to monitor effluents and other manufacturing by-products, which are often disposed of by discharging into rivers or the like. For example, in the petrochemical industry, the hydrocarbon content of waste waters must be closely monitored so as to avoid discharging toxic effluent into rivers or estuaries. Similarly in the manufacture of herbicides, there is a potential for the formation of carcinogenic nitrosamines. Such manufacturing processes therefore require careful monitoring.

There is a range of techniques which utilize analytical apparatus to monitor (qualitatively or quantitatively) a particular analyte, such as an organic compound, present in a sample of a fluid. Examples of such techniques include gas chromatography and infra-red spectrometry. The analytical methods currently available employ multi-stage procedures in order to provide an accurate analysis of the sample to be tested. Firstly it is necessary to mix the sample in a solvent and subsequently extract the analyte from the mixture. The next stage is to collect the analyte using a separation medium such as, for example, trapping the analyte onto a solid surface such as in packed column chromatography, so that the analyte is substantially pure and can be analyzed accurately. Once the analyte is eluted from the separation medium it may be analyzed using various types of analytical apparatus, such as gas spectrometers, infra-red spectrometers, or the like.

A further disadvantage of using such traditional extraction techniques is that they generally require the use of organic solvents. The use of organic solvents industrially is now being restricted by legislation, such that users may be required to justify the purchase of some solvent i.e. some solvent such as carbontetrachloride or Freon 113 can only be supplied if their use falls within the essential use category.

Supercritical fluids have previously been used as alternatives to organic solvents in extraction of analytes from a fluid. In particular, the technique of supercritical fluid extraction provides an effective method for extracting materials, such as complex high molecular weight mixtures which are difficult to separate. Supercritical fluid extraction generally utilizes a mobile phase of highly compressed gas at or above its critical temperature and pressure. When such compounds are subjected to extremes of pressure and temperature, they enter a supercritical state being neither fluid nor gas. Examples of such supercritical fluids include carbon dioxide, toluene, ammonia, fluorinated hydrocarbons, nitric oxide, sulfur fluoride, helium and xenon. A complete review of supercritical fluid extraction and its applications is disclosed in Anal. Chem 1994, 66 106R–130R. Supercritical fluid extraction is also a multi-stage technique requiring firstly extraction of the analyte from the sample and secondly separation of the analyte from the supercritical fluid. The analyte is finally collected and analyzed by, for example, infra-red spectroscopy.

OBJECTS OF THE INVENTION

It is an object of the present invention to provide analytical apparatus which obviates chromatographic separation.

It is a further object of the invention to provide apparatus which can enable accurate monitoring of compounds such as hydrocarbons, present in a fluid sample which is to be analyzed.

SUMMARY OF THE INVENTION

The invention comprises apparatus for monitoring one or more analytes present in a fluid sample, which comprises:
(a) an extraction chamber shaped and dimensioned to receive a sample receptacle for a fluid sample such that at least one analyte can be extracted from the fluid sample by supercritical fluid extraction;
(b) a removable cover member shaped and dimensioned to permit introduction of the receptacle into the extraction chamber;
(c) an analysis cell having a window which is substantially transparent to infra-red radiation and permits infra-red radiation from an external infra-red source to pass through extracted analyte to means for analyzing the infra-red radiation; and
(d) means for permitting communication between the extraction chamber and the analysis cell.

The sample to be analyzed may be in a contaminated solution, present in a solid matrix such as soil, or on the surface of a solid, such as steel.

Preferably the analyzing means includes an infra-red spectrometer arranged to analyze infra-red radiation passed through the extracted analyte. Thus advantageously the apparatus may be used not only to provide a quantitative indication of compounds present, but also a qualitative indication of the types of compound present in the fluid sample.

Preferably, the apparatus includes a vortex mixer for creating a vortex of the supercritical fluid and the analyte in the chamber.

Preferably, the vortex mixer is arranged to introduce into the extraction chamber a non-supercritical fluid which is to be converted into the supercritical fluid. Advantageously, the vortex mixer promotes efficient extraction and prevents water droplets from reaching the analysis cell.

The extraction chamber includes a removable cover member arranged to allow the sample receptacle to be introduced into the extraction chamber. Such a sample receptacle preferably has a volume in the range 100 to 3000 ml, and preferably permits substantially all the analyte to be extracted from the fluid sample and transferred to the extraction chamber. The invention provides the advantage that significant amounts of analyte are not left behind, as would happen if the contents of the sample receptacle were first transferred to the extraction chamber prior to analysis. Such erroneously transferred material would be accounted for in the infra-red analysis.

Desirably, the apparatus includes a solid phase sorbent trap arranged between said extraction chamber and said analysis cell. The solid phase sorbent trap may contain a material such as the material commercially available as "Florisil".

Desirably, the apparatus includes a demisting chamber arranged between said extraction chamber and said analysis cell.

The apparatus advantageously obviates the need for chromatographic separation phase making analysis of a fluid sample quicker and easier. When the sample of fluid is mixed with the supercritical fluid, under the extremes of temperature and pressure the compounds are dissolved in the supercritical fluid which may then be collected in the collection chamber for subsequent analysis by, for example, the infra-red spectrometer.

Preferably, the apparatus includes means to provide the pressure required to reach and maintain said supercritical fluid in its supercritical state. In the present invention the temperature of the fluid is maintained at or near its critical point. "Near" in this context generally means up to 100° C. above the critical point of the fluid. For example, for $CO_2$ the critical point temperature is 31.3° C., so the preferred range is from 31.3° C. to 131.3° C.

Preferably the apparatus includes a baffle arrangement arranged to allow the extracted analyte and the supercritical fluid to pass from the extraction chamber to the analysis cell while substantially preventing transfer of water from the extraction chamber to the analysis cell. Further preferably the baffle arrangement comprises one or more chicane-type baffles of stainless steel. The baffles substantially alleviate water splashback or aerosol droplets accumulating on the windows of the analysis cell.

Preferably, the infra-red source comprises interfacing fiber optic links adjacent one of said windows of said analysis cell. Further preferably, the fiber optic links are contained within a temperature regulated housing.

It is preferred that the apparatus includes heating means arranged to surround the extraction chamber and the analysis cell, thus ensuring the complete housing is kept at the temperature necessary to maintain the supercritical fluid (such as carbon dioxide) in its supercritical state. A pressure transducer may also be connected to the apparatus so as to provide an indication of pressure in the housing.

It is also preferred that the apparatus includes heating means for said window of said analysis cell thus substantially alleviating accumulation of water droplets or mist or the like on the window. Preferably the apparatus contains two windows for the analysis cell, the windows being arranged to allow the infra-red radiation from the radiation source to pass into and through the analysis cell.

According to a second aspect of the present invention there is provided a method for monitoring one or more analytes present in a fluid sample, which method comprises:
(a) providing a sample receptacle containing the fluid sample;
(b) introducing the sample receptacle into an extraction chamber;
(c) extracting in the extraction chamber at least one analyte from the fluid sample in the receptacle by supercritical fluid extraction;
(d) permitting direct communication of extracted analyte from said extraction chamber to an analysis cell; and
(e) infra-red analysis of extracted analyte in the analysis cell.

Desirably, the infra-red analysis is by an infra-red spectrometer.

Preferably, the supercritical fluid comprises supercritical carbon dioxide. Advantageously, supercritical carbon dioxide is transparent over a wide portion of the mid infra-red spectrum. Therefore, although supercritical carbon dioxide may be present in the analysis cell, accurate monitoring of the extracted compounds is substantially unaffected.

For some types of analytes, the supercritical fluid may contain up to 30% of a modifying fluid. Preferably, the modifying fluid comprises an aliphatic alcohol.

Preferably, the fluid sample contains at least one hydrocarbon. In some embodiments, the analyte may be thermally labile.

Desirably, the analyte comprises substantially non-polar hydrocarbons from which polar organic compounds have been removed prior to the extraction.

It is preferred that water present is substantially removed from the extracted analyte and supercritical fluid before the extracted analyte and supercritical fluid enter the analysis cell.

It is also preferred that separation means comprise a baffle arrangement, which comprises one or more chicane-type baffles of stainless steel.

Preferably, the sample of fluid is mixed initially with liquid carbon dioxide in the extraction chamber, the temperature inside the chamber being subsequently adjusted to convert the carbon dioxide to its supercritical state.

BRIEF DESCRIPTION OF THE DRAWING

The invention will now be described, by way of example only, with reference to the accompanying drawings, wherein the sole FIGURE is a detailed cross section of the apparatus according to the invention.

DETAILED DESCRIPTION OF THE PREFERRED EMBODIMENTS

Referring to the drawing, there is illustrated apparatus for monitoring compounds present in a fluid, which apparatus is generally indicated by the reference numeral 1. The apparatus comprises an extraction chamber 2 for extracting compounds, such as hydrocarbons, from the fluid sample 3. The fluid sample 3 is contained in a sample bottle 4, which is inserted into the extraction chamber 2, via a removable cover member 5. Removable cover member 5 is connected to extraction chamber 2 by complementary thread 15a and 15b.

A vortex mixer 6 is arranged to introduce carbon dioxide into the sample bottle 4. The apparatus 1 also comprises a FTIR analysis cell 14. The analysis cell 14 has two mutually opposed windows on opposite sides of the analysis cell, which windows are transparent to infra-red radiation emitted from an infra-red source. The analysis cell 14 further comprises a heater to prevent accumulation of water droplets or the like on the surface of the windows.

The extraction chamber 2 further comprises stainless steel baffles 7 to prevent further potential accumulation of water droplets or mist on the windows of the analysis cell.

A demisting chamber is sited between the extraction chamber 2 and the analysis cell 14. A solid phase sorbent trap 9 is also sited between the demisting chamber 8 and the analysis cell 14. This is in order that extracted polar organics may be removed prior to the analysis of non-polar hydrocarbons.

The analysis cell 14 is fitted with an expansion chamber 10. The expansion chamber 10 is fitted with an inlet valve 11 and a vent valve 12, to facilitate operation. A HPLC high pressure valve 13, is sited between the extraction vessel and the analysis cell, to enable either valve loop injections or pumping of water-miscible organic solvent, such as acetone, to wash the analysis cell windows and/or to displace trapped polar organic compounds from a solid phase sorbent trap.

In use, the sample fluid to be analyzed is collected in sample bottle 4, which is then introduced into the extraction chamber 2 via the removable cover member 5. The vortex mixer 6 is then used to introduce carbon dioxide into the sample container 4 which is placed inside the extraction chamber 2. The use of the vortex mixer reduces the quantity of water aerosol droplets reaching the analysis cell windows.

The stainless steel baffles 7 complements the vortex mixer 6. When the temperature and pressure levels are raised sufficiently inside the extraction chamber 2, the carbon dioxide enters the supercritical state. The compounds in the fluid sample 3 are dissolved in the supercritical fluid and circumvent the baffle arrangement 7 to enter the analysis cell 14. Both the supercritical carbon dioxide and the extracted compound enter the analysis cell 14, but the infra-red spectrum of the supercritical fluid is transparent over a wide portion of the mid infra-red spectrum so that the infra-red spectrum of the extracted compound(s) is substantially unaffected by the presence of the supercritical carbon dioxide. The infra-red source emits a beam of radiation which passes initially through one of the windows and through the extracted compound(s). The infra-red beam exits the collection chamber through a second window where the infra-red spectrum of the extracted compound(s) can be analyzed by an infra-red spectrometer. The infra-red spectrometer is connected to a microprocessor which enables the spectrum to be observed on a cathode ray tube or displayed on a computer screen or the like.

I claim:

1. Apparatus for monitoring at least one analyte present in a fluid sample, which apparatus comprises:
    (a) an extraction chamber and an open sample receptacle for containing said fluid sample, said extraction chamber being shaped and dimensioned to define an interior volume for containing a supercritical fluid and said a sample receptacle, wherein the interior volume of the extraction chamber is in fluid communication with the open sample receptacle such that said at least one analyte can be extracted from said fluid sample by supercritical fluid extraction;
    (b) a removable cover member shaped and dimensioned to permit introduction of said receptacle into said extraction chamber;
    (c) an analysis cell having a window which is substantially transparent to infra-red radiation and permits infra-red radiation from an external infra-red source to pass through said extracted analyte to means for analyzing said infra-red radiation; and
    (d) means for permitting communication between the interior volume of said extraction chamber and said analysis cell.

2. Apparatus according to claim 1, wherein said sample receptacle has a volume in the range 100 to 3000 ml.

3. Apparatus according to claim 1, which includes an infra-red spectrometer arranged to analyze infra-red radiation passed through said extracted analyte in said analysis cell.

4. Apparatus according to claim 1, which includes a vortex mixer for creating a vortex of said supercritical fluid and said analyte in said extraction chamber.

5. Apparatus according to claim 4, wherein said vortex mixer is arranged to introduce into said extraction chamber a non-supercritical fluid which is to be converted into said supercritical fluid.

6. Apparatus according to claim 1, which includes a solid phase sorbent trap arranged in said communication means between said extraction chamber and said analysis cell.

7. Apparatus according to claim 1, which includes a demisting chamber arranged between said extraction chamber and said analysis cell.

8. Apparatus according to claim 1, which includes means to provide a predetermined pressure required to reach and maintain said supercritical fluid in its supercritical state.

9. Apparatus according to claim 1, which includes a baffle arrangement arranged to allow said extracted analyte and said supercritical fluid to pass from said extraction chamber to said analysis cell while substantially preventing transfer of water from said extraction chamber to said analysis cell.

10. Apparatus according to claim 9, wherein said baffle arrangement comprises one or more chicane-type baffles of stainless steel.

11. Apparatus according to claim 1, which includes an infra-red source comprising interfacing fiber optic links adjacent said window.

12. Apparatus according to claim 11, further comprising a temperature regulated housing containing said fiber optic links.

13. Apparatus according to claim 1, which includes heating means arranged to surround said extraction chamber and said analysis cell.

14. Apparatus according to claim 1, which includes heating means for said window.

15. Apparatus according to claim 1, in which said analysis cell contains two said windows, said windows being arranged to allow said infra-red radiation from said radiation source to pass into and through said analysis cell.

16. Apparatus according to claim 1, which includes an expansion chamber for said analysis cell.

17. A method for monitoring one or more analytes present in a fluid sample, which method comprises:
    (a) providing an open sample receptacle containing said fluid sample;
    (b) introducing said sample receptacle into an extraction chamber, the extraction chamber defining an interior volume for containing a supercritical fluid and said sample receptacle;
    (c) extracting in said extraction chamber at least one analyte from said fluid sample in said receptacle by supercritical fluid extraction;
    (d) permitting direct communication of extracted analyte from the interior volume of said extraction chamber to an analysis cell; and
    (e) performing infra-red analysis of extracted analyte in said analysis cell.

18. A method according to claim 17, wherein said infra-red analysis is by an infra-red spectrometer.

19. A method according to claim 17, wherein said supercritical fluid comprises supercritical carbon dioxide.

20. A method according to claim 17, wherein said supercritical fluid contains up to 30% of a modifying fluid.

21. A method according to claim 20, wherein said modifying fluid comprises an aliphatic alcohol.

22. A method according to claim 17, wherein said fluid sample contains at least one compound selected from a hydrocarbon and a thermally labile compound.

23. A method according to claim 17, wherein said analyte comprises substantially non-polar hydrocarbons from which polar organic compounds have been removed prior to said extraction.

24. Apparatus for monitoring at least one analyte present in a fluid sample, which apparatus comprises:
    (a) an extraction chamber shaped and dimensioned to receive a sample receptacle for said fluid sample such that said at least one analyte can be extracted from said fluid sample by supercritical fluid extraction;

(b) a removable cover member shaped and dimensioned to permit introduction of said receptacle into said extraction chamber;
(c) an analysis cell having a window which is substantially transparent to infra-red radiation and permits infra-red radiation from an external infra-red source to pass through said extracted analyte to means for analyzing said infra-red radiation;
(d) means for permitting communication between said extraction chamber and said analysis cell; and
(e) a baffle arrangement arranged to allow said extracted analyte and said supercritical fluid to pass from said extraction chamber to said analysis cell while substantially preventing transfer of water from said extraction chamber to said analysis cell.

25. Apparatus according to claim 24, wherein said baffle arrangement comprises one or more chicane-type baffles of stainless steel.

* * * * *